United States Patent
Eden et al.

(10) Patent No.: US 7,482,750 B2
(45) Date of Patent: Jan. 27, 2009

(54) PLASMA EXTRACTION MICROCAVITY PLASMA DEVICE AND METHOD

(75) Inventors: J. Gary Eden, Mahomet, IL (US); Sung-Jin Park, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 410 days.

(21) Appl. No.: 11/344,514

(22) Filed: Jan. 31, 2006

(65) Prior Publication Data

US 2007/0108910 A1    May 17, 2007

Related U.S. Application Data

(63) Continuation-in-part of application No. 11/042,228, filed on Jan. 25, 2005.

(60) Provisional application No. 60/648,504, filed on Jan. 31, 2005.

(51) Int. Cl.
    *H01J 17/49*    (2006.01)
(52) U.S. Cl. .................................. 313/582; 257/211
(58) Field of Classification Search ................. 313/631, 313/581, 618, 582–587; 257/211
    See application file for complete search history.

(56) References Cited

U.S. PATENT DOCUMENTS

| | | | | |
|---|---|---|---|---|
| 4,763,187 A * | 8/1988 | Biberian | ...................... | 348/796 |
| 5,583,344 A * | 12/1996 | Mizumura et al. | ...... | 250/492.21 |
| 6,016,027 A * | 1/2000 | DeTemple et al. | ........... | 313/356 |
| 6,194,833 B1 * | 2/2001 | DeTemple et al. | ........... | 313/631 |
| 6,346,770 B1 * | 2/2002 | Schoenbach et al. | ........ | 313/491 |
| 2003/0080664 A1 * | 5/2003 | Eden et al. | .................... | 313/356 |
| 2003/0080688 A1 * | 5/2003 | Eden et al. | ................ | 315/169.3 |
| 2003/0132693 A1 * | 7/2003 | Eden et al. | .................... | 313/356 |
| 2006/0084262 A1 | 4/2006 | Qin | | |

OTHER PUBLICATIONS

S.J. Park & J.G. Eden, "Carbon nanotube-enhanced performance of microplasma device," May 31, 2004, Applied Physics Letters, vol. 84, No. 22; p. 4481-4483.*

S.J. Park, C.J. Wagner, & J.G. Eden, "Performance of Microdischarge devices and arrays with screen electrodes," Jan. 2001, IEEE Photonics Technology Letters, vol. 13, No. 1, p. 61-63.*

(Continued)

*Primary Examiner*—Toan Ton
*Assistant Examiner*—Hana A Sanei
(74) *Attorney, Agent, or Firm*—Greer, Burns & Crain, Ltd.

(57) ABSTRACT

A preferred embodiment plasma extraction microcavity plasma device generates a spatially-confined plasma in a gas or vapor, or gas and vapor mixture, including, for example, atmospheric pressure air. A microcavity plasma device is excited by a potential applied between excitation electrodes of the microcavity plasma device, and a probe electrode proximate the microcavity is maintained at the potential of one of the electrodes, extracts plasma from the microcavity plasma device. In preferred embodiments, the excitation electrodes of the microcavity plasma device are isolated from the plasma by dielectric, and time-varying (AC, RF, bipolar or pulsed DC, etc.) potential excites a plasma that is then extracted by the probe electrode. In alternate embodiments, the microcavity plasma device has an excitation electrode that contacts the plasma. A DC potential excites a plasma that is then extracted by the probe electrode.

16 Claims, 8 Drawing Sheets

OTHER PUBLICATIONS

S.J. Park, J. Chen, C. Lui & J.G. Eden, "Silicon microdischarge devices having inverted pyramidal cathodes: Fabrication and performance of arrays," Jan. 22, 2001, Applied Physics Letters, vol. 78, No. 4, p. 419-421.*

* cited by examiner

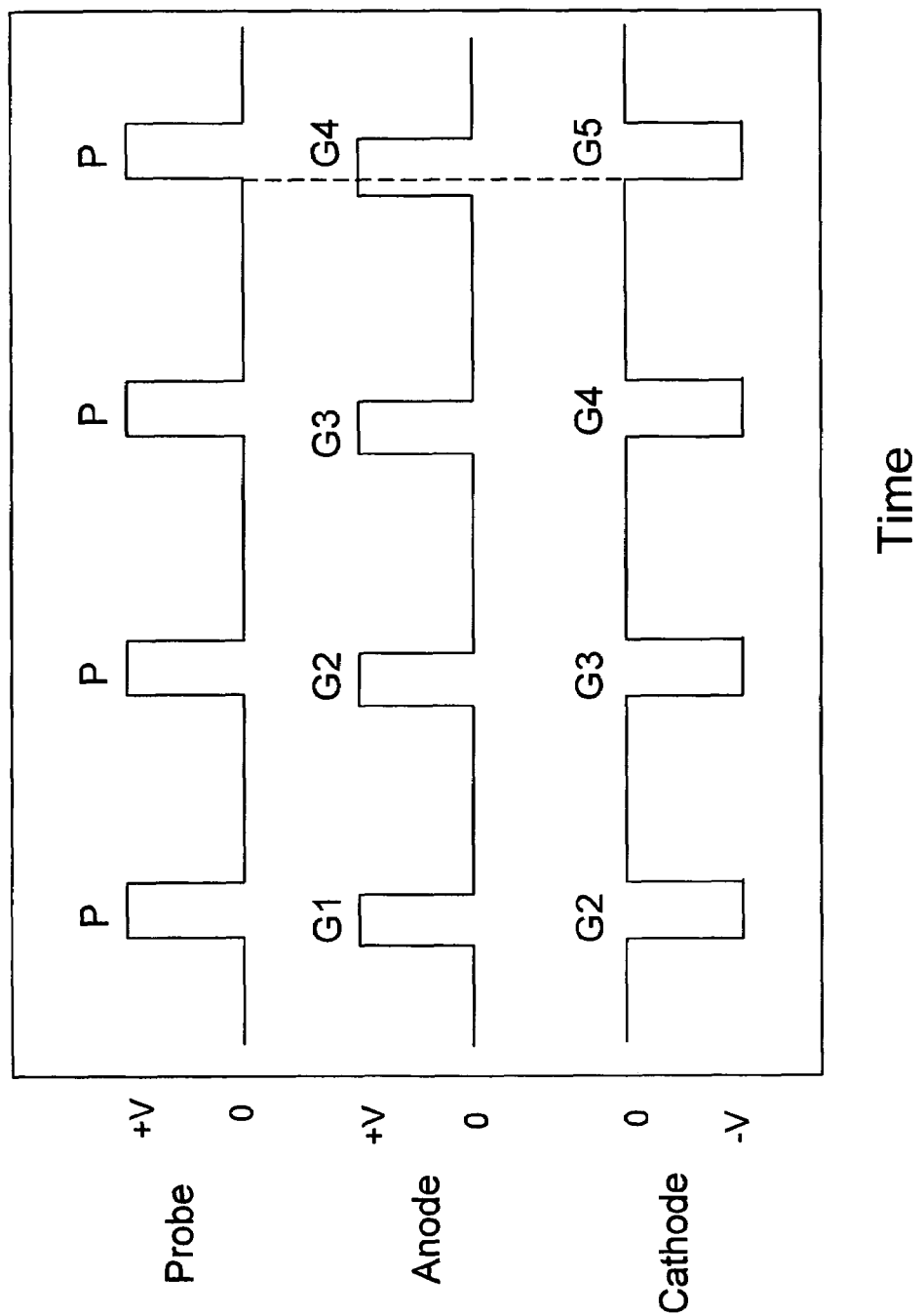

PLASMA EXTRACTION MICROCAVITY PLASMA DEVICE AND METHOD

PRIORITY CLAIM AND REFERENCE TO RELATED APPLICATIONS

This application claims priority under 35 U.S.C. 119 from provisional application Ser. No. 60/648,504 filed on Jan. 31, 2005. This application is also a continuation-in-part and claims priority under 35 U.S.C §120 from pending application Ser. No. 11/042,228 filed on Jan. 25, 2005.

STATEMENT OF GOVERNMENT INTEREST

This invention was made with Government assistance under U.S. Air Force Office of Scientific Research grant No. F49620-03-1-0391. The Government has certain rights in this invention.

FIELD OF THE INVENTION

The present invention relates to microcavity plasma devices, also known as microdischarge or microplasma devices, and in particular to plasma extraction microcavity plasma devices and methods.

BACKGROUND

Microcavity plasmas, plasmas confined to a cavity with a characteristic spatial dimension <1 mm, have several distinct advantages over conventional, macroscopic discharges. For example, the small physical dimensions of microcavity plasma devices allow them to operate at gas or vapor pressures much higher than those accessible to a macroscopic discharge such as that produced in a fluorescent lamp. When the diameter of the microcavity of a cylindrical microplasma device is, for example, on the order of 200-300 µm or less, the device is capable of operating at pressures as high as atmospheric pressure and beyond. In contrast, standard fluorescent lamps operate at pressures typically less than 1% of atmospheric pressure. Also, microplasma devices may be operated with different discharge media (gases, vapors or combinations thereof) to yield emitted light in the visible, ultraviolet, and infrared portions of the spectrum. Another unique feature of microplasma devices, the large power deposition into the plasma (typically tens of kW/cm$^3$ or more), is partially responsible for the efficient production of atoms and molecules that are well-known optical emitters. Consequently, because of the properties of microplasma devices, including the high pressure operation mentioned above and their electron and gas temperatures, microplasmas are efficient sources of optical radiation.

Research by the present inventors and colleagues at the University of Illinois has pioneered and advanced the state of microcavity plasma devices. This work has resulted in practical devices with one or more important features and structures. For example, semiconductor fabrication processes have been adopted to demonstrate densely packed arrays of microplasma devices exhibiting uniform emission characteristics. Arrays fabricated in silicon comprise as many as 250,000 microplasma devices in an active area of 25 cm$^2$, each device in the array having an emitting aperture of typically 50 µm×50 µm.

The following U.S. patents and patent applications describe microcavity plasma devices resulting from these research efforts. Published Applications: 20050148270—Microdischarge devices and arrays; 20040160162—Microdischarge devices and arrays; 20040100194—Microdischarge photodetectors; 20030132693—Microdischarge devices and arrays having tapered microcavities; U.S. Pat. No. 6,867,548—Microdischarge devices and arrays; U.S. Pat. No. 6,828,730—Microdischarge photodetectors; U.S. Pat. No. 6,815,891—Method and apparatus for exciting a microdischarge; U.S. Pat. No. 6,695,664—Microdischarge devices and arrays; U.S. Pat. No. 6,563,257—Multilayer ceramic microdischarge device; U.S. Pat. No. 6,541,915—High pressure arc lamp assisted start up device and method; U.S. Pat. No. 6,194,833—Microdischarge lamp and array; U.S. Pat. No. 6,139,384—Microdischarge lamp formation process; and U.S. Pat. No. 6,016,027—Microdischarge lamp.

U.S. Pat. No. 6,541,915 discloses arrays of microcavity plasma devices in which the individual devices are mounted in an assembly that is machined from materials including ceramics. Metallic electrodes are exposed to the plasma medium which is generated within a microcavity and between the electrodes. U.S. Pat. No. 6,194,833 also discloses arrays of microcavity plasma devices, including arrays for which the substrate is ceramic and a silicon or metal film is formed on it. Electrodes formed at the tops and bottoms of cavities, as well as the silicon, ceramic (or glass) microcavities themselves, contact the plasma medium. U.S. Published Patent Application 2003/0230983 discloses microcavity plasmas produced in low temperature ceramic structures. The stacked ceramic layers are arranged and micromachined so as to form cavities and intervening conductor layers excite the plasma medium. U.S. Published Patent Application 2002/0036461 discloses hollow cathode discharge devices in which electrodes contact the plasma/discharge medium.

Additional exemplary microcavity plasma devices are disclosed in U.S. patent application Ser. No. 10/829,666, filed Apr. 22, 2004, entitled "Phase Locked Microdischarge Array and AC, RF, or Pulse Excited Microdischarge"; U.S. patent application Ser. No. 10/984,022, filed Nov. 8, 2004, entitled "Microplasma Devices Excited by Interdigitated Electrodes;" U.S. patent application Ser. No. 10/958,174, filed on Oct. 4, 2004, entitled "Microdischarge Devices with Encapsulated Electrodes,"; U.S. patent application Ser. No. 10/958,175, filed on Oct. 4, 2004, entitled "Metal/Dielectric Multilayer Microdischarge Devices and Arrays"; and U.S. patent application Ser. No. 11/042,228, entitled "AC-Excited Microcavity Discharge Device and Method."

Producing plasmas with glow discharge in room air has been notoriously difficult but the ability to do so in a compact, low power device can have profound implications for, for example, environmental analysis of air samples. A direct current glow discharge has been reported. See, A.-A. H. Mohamed, R. Block, and K. H. Schoenbach, Direct Current Glow discharges in Atmospheric Air" IEEE Trans. Plasma Sci. 30, 182 (2002); Stark & Shoenbach; "Direct Current Glow Discharges in Atmospheric Air". In those papers, it is reported that glow discharges were generated in atmospheric air by using a direct current diameter microcavities hollow cathode discharge as a plasma cathode. The microcavities ranged from 80 µm to 130 µm. Electrodes were molybdenum foils separated by dielectric. A third planar electrode extracts discharge glow. Glow discharges extending over distances up to 2 cm were produced, but doing so required a third electrode positively biased with respect to the microcavity cathode discharge. Sustaining voltages of the hollow cathode device ranged from 400-600 V, while the third planar electrode was maintained at 250V. See, Stark & Shoenbach, Appl. Phys. Lett., Vol. 74, No. 25 at 3770-71. Extracted discharge glows expanded well beyond the diameter of the discharge devices. The papers report that the bias voltage increases linearly with gap length. It was also observed that the size (cross-sectional area) of the plasma changed with distance from the microhollow cathode and its diameter increased to a value much larger than the transverse dimension of the microhollow cathode. The transverse spreading of the plasma was used to accomplish the merging two plasmas to form a homogeneous, large volume plasma.

SUMMARY OF THE INVENTION

A preferred embodiment plasma extraction microcavity plasma device generates a spatially-confined plasma in a gas or vapor, or gas and vapor mixture, including, for example, atmospheric pressure air. A microcavity plasma device is excited by a potential applied between excitation electrodes of the microcavity plasma device, and a probe electrode proximate the microcavity is maintained at the potential of one of the electrodes, extracts plasma from the microcavity plasma device. In preferred embodiments, the excitation electrodes of the microcavity plasma device are isolated from the plasma by dielectric, and time-varying (AC, RF, bipolar or pulsed DC, etc.) potential excites a plasma that is then extracted by the probe electrode. In alternate embodiments, the microcavity plasma device has an excitation electrode that contacts the plasma. A DC potential excites a plasma that is then extracted by the probe electrode.

BRIEF DESCRIPTION OF THE DRAWINGS

FIG. 8 shows an exemplary timing diagram for operation of the device of FIG. 7.

DETAILED DESCRIPTION OF THE PREFERRED EMBODIMENTS

Figure 1:
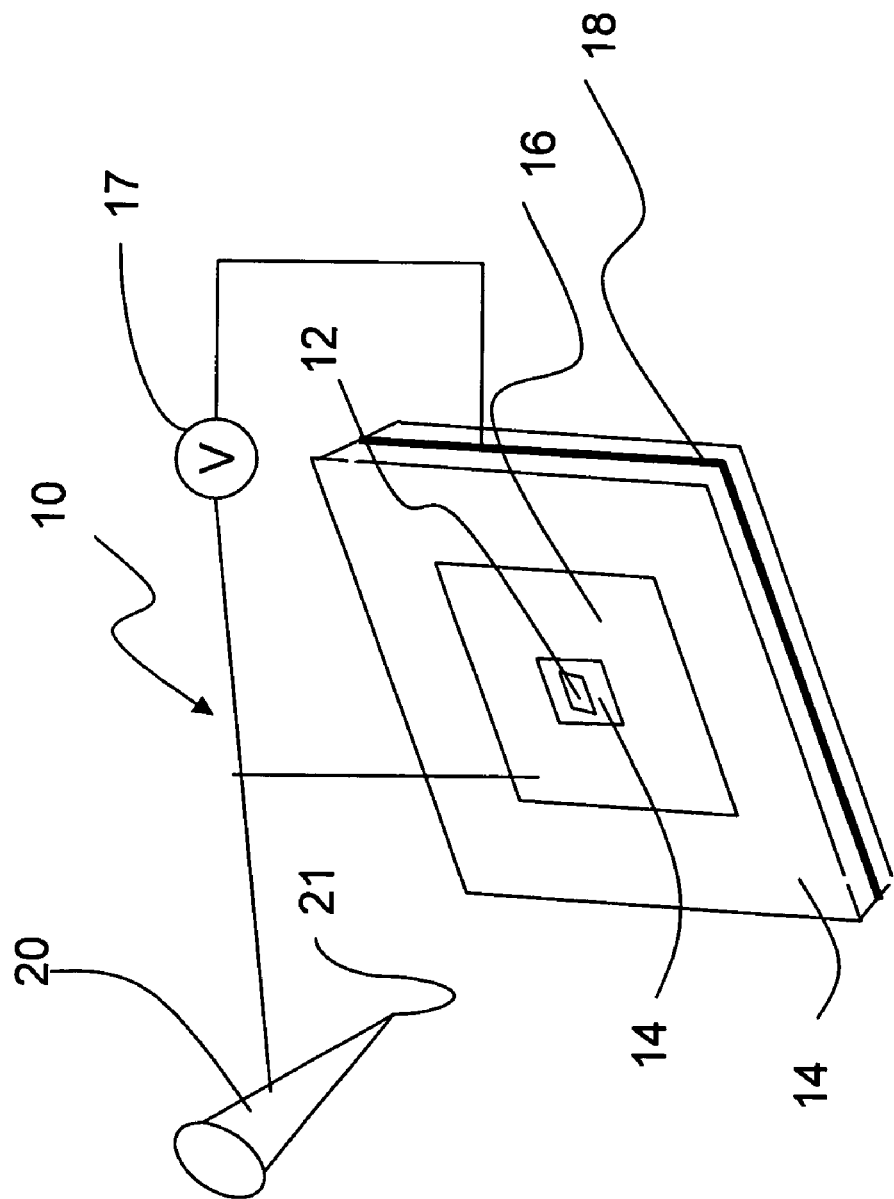
FIG. 1 is a perspective schematic view of a preferred embodiment plasma extraction microcavity plasma device.

A preferred embodiment plasma extraction microcavity plasma device generates a spatially-confined plasma in a gas or vapor, or gas and vapor mixture, including, for example, atmospheric pressure air. A microcavity plasma device is excited by a potential applied between excitation electrodes of the microcavity plasma device, and a probe electrode proximate the microcavity is maintained at the potential of one of the electrodes, extracts plasma from the microcavity plasma device. In preferred embodiments, the excitation electrodes of the microcavity plasma device are isolated from the plasma by dielectric, and AC time-varying (AC, RF, bipolar or pulsed DC, etc.) potential excites a plasma that is then extracted by the probe electrode. In alternate embodiments, the microcavity plasma device has an excitation electrode that contacts the plasma. A DC potential excites a plasma that is then extracted by the probe electrode.

In operation of devices of the invention, the probe electrode is maintained at the same potential as one electrode of the device and positioned proximately to the microcavity plasma. The probe extracts plasma from the device and generates a stable, uniform plasma in a gas or vapor, or mixture of gas and vapor.

Devices of the invention can operate in atmospheric pressure air. Surprisingly, a stable, uniform plasma can be induced in atmospheric pressure air when the probe electrode is positioned up to approximately 1.0 mm from the microcavity opening. Further, the cross-sectional dimensions of this stable, uniform plasma are confined. Specifically, the cross-sectional dimensions of the plasma are not substantially larger than the dimensions of the microcavity opening. That is, the discharge produced between the probe electrode and microdischarge is spatially-confined along its length to a cross-sectional area determined by the microcavity.

Devices of the invention produce and extract a stable, uniform plasma. The probe electrode is a conductor or semiconductor, and can assume a variety of probe shapes and sizes. The probe electrode is preferably coated with dielectric, and the microcavity plasma device is preferably an AC microcavity plasma device, i.e., a device with excitation electrodes that are isolated from the microcavity by dielectric and that is excited by a time-varying voltage (AC-sinusoidal, RF, bioploar, pulsed DC, etc.). The microcavity plasma device is preferably a microplasma device having an inverted pyramid microcavity fabricated in silicon. The device can be fabricated by standard semiconductor fabrication techniques. Additional embodiment devices include arrays of microcavities and arrays of probe electrodes. In another exemplary embodiment, a probe electrode is connected to a mover and acts as both a probe electrode and valve.

The invention provides a method for producing and extracting a plasma in a gas or vapor, or a mixture of gas and vapor. A preferred embodiment method produces and extracts a plasma from a microcavity plasma device operating in atmospheric pressure air. A probe electrode is positioned proximately to the opening of a microcavity in a microcavity plasma device. A potential is applied between excitation electrodes of the microcavity plasma device and the probe electrode is maintained at the same potential as a device electrode. A plasma is ignited in the device microcavity. The probe electrode extracts plasma creating a stable, uniform plasma.

Preferred embodiments will now be discussed with respect to the drawings. The drawings include schematic figures, which will be fully understood by skilled artisans with reference to the accompanying description. Features may be exaggerated for purposes of illustration. From the preferred embodiments, artisans will recognize broader aspects of the invention.

FIG. 1 shows a plasma extraction microcavity plasma device 10 according to an embodiment of the invention. A microcavity 12 is formed in a substrate 14. An excitation electrode 16 is positioned adjacent to the microcavity opening. An appropriate voltage 17 applied between the excitation electrode and another excitation electrode 18. The excitation electrode 18 is shown as a layer, such as a metal layer, disposed within the substrate. The excitation electrode 18 can be patterned, e.g., it can surround the microcavity, be patterned to be adjacent the microcavity 12, form separate electrodes, etc. It can also be below the microcavity 12.

In other embodiments, the excitation electrodes 16 and 18 are coplanar electrodes buried within the substrate. While one microcavity 12 is shown, there can be an array of microcavities, and the microcavities can be excited as a group, or can be addressable in groups or individually. In embodiments, electrodes 16, and 18 are separately addressable, and the substrate 14 is part of an integrated electronic device. In preferred embodiments, the substrate 14 is silicon and the microcavity is an inverted pyramidal microcavity. In preferred embodiments, the electrodes 16, 18 are isolated from the microcavity. This isolation prolongs device life.

Specifically, the excitation electrodes 16, 18 in preferred embodiments are isolated from the microcavity 12 by dielectric, and the voltage 17 is an AC time varying voltage (e.g., AC-sinusoidal, RF, bipolar, pulsed DC, etc.). In other embodiments, the electrodes 16, 18 are exposed to the microcavity and the voltage 17 is a DC voltage.

A probe electrode 20 is positioned proximately to the microcavity 12 with a small gap from a tip 21 of the probe 20 to the microcavity 12. The probe electrode 20 is connected to and/or maintained at substantially the same potential as one of the excitation electrodes 16, 18. Also the top electrode 18 can be floating. While one probe electrode is shown, other embodiments include arrays of probe electrodes, and there can be a one-to-one correspondence between probe electrodes, or other arrangements in which one probe electrode corresponds to more than one microcavity or vice versa.

With gas or vapor, or mixture of gas and vapor (including multiple gases and/or multiple vapors) in the microcavity 12 as well as the region between the microcavity and the probe electrode, plasma is formed in the microcavity 12 for with an appropriate value of applied voltage. Plasma is also extracted from the microcavity despite the fact that probe electrode 20 is maintained at the same potential one of the excitation electrodes 16, 18. Furthermore, the plasma column, or conduit, produced between the microcavity 12 and the probe electrode 20 is spatially-confined in the dimension transverse to the axis defined by the probe electrode tip and the center of the microcavity 12.

In specific embodiments of the invention, an array of microcavity plasma devices, as are known in the art, can produce plasma to be extracted by a probe electrode or by an array of probe electrodes. The microcavity may be, for example, shaped as an inverted pyramid or may be trapezoidal, rectangular or cylindrical in cross section. The probe electrode can assume a variety of shapes and sizes. The probe electrode may be a conductor or semiconductor. The probe electrode is preferably coated with dielectric.

In exemplary embodiments consistent with the device of FIG. 1, the probe electrode 20 has a tip 21 of dimension ranging from 1 to 50 μm. The gap between the probe electrode 20 and the microcavity 12 can range from approximately 100 μm to at least a millimeter. The time varying voltage waveform that excites the microdischarge can be AC-sinusoidal, pulsed DC, bipolar, etc. Diffuse microplasmas can be produced in atmospheric pressure air or in another gas or vapor or in a gas or vapor at a pressure that differs from atmospheric pressure. The electrodes and microcavity interior surface of the microdischarge devices may be covered, in whole or in part, by dielectric layers to extend their lifetimes. For example, a silicon nitride film (grown by low pressure chemical vapor deposition) covering a Si cavity may be employed. As another example, the probe electrode 20 may be coated with an exceptionally robust dielectric, such as a film of diamond or boron nitride, in order to prolong the life of the entire device.

In a specific embodiment of the invention, the substrate 14 is Si and the microcavity 12 is an inverted pyramid with a (50 μm)$^2$ square aperture at its base. Excitation electrodes 16, 18 can be metal. In another embodiment, a semiconductor substrate 14 forms one of the excitation electrodes.

The probe electrode 20 can be situated approximately 0.5 mm from the anode and can be formed of metal, such as Ni or cobalt steel, or, in some embodiments, a semiconductor. The probe electrode 20 is preferably coated with dielectric. The probe electrode 20 may be formed with a tip of cross-sectional area ~3×10$^{-3}$ mm$^2$. An example excitation, voltage, a sinusoidal AC voltage of 600-800 volts (peak-to-peak) with a frequency from 5 kHz to 20 kHz can be applied across the microdischarge device. A stable plasma of uniform cross-section that is dimensioned similarly to the microcavity 12 will be produced in the microcavity 21 and extracted into the gap between the probe electrode tip 21 and the microcavity 12.

A prototype device consistent with FIG. 1 used a probe electrode having a dielectric tip. An AC voltage was applied across the microdischarge device electrodes with an excitation frequency of 5 kHz. The plasma between the microcavity and the probe tip had a cross-sectional shape of substantially the diameter of the microcavity. Ignition of the plasma occurred at a voltage of approximately 650 volts (peak-to-peak value; RMS voltage ≅230 V). Another prototype device used a probe electrode having a metal tip and a plasma was excited and extracted at an excitation frequency of 20 kHz. The gap from the probe electrode to the microdischarge device was approximately 1 mm. Ignition of the plasma occurred at a peak-to-peak voltage of approximately 750 volts ($V_{RMS}$=265 V). The discharges were stable and spatially uniform, producing a diffuse glow in air.

In preferred embodiments of the invention, the light from the plasma produced in any embodiments of the invention can be coupled into an optical transmission device, such as an optical fiber. The light emission from the discharge can then be coupled into an analytical instrument, such as a spectrograph, for analysis of the gas or vapor in which the discharge occurs. The size of the plasma makes coupling the emission into either a multimode, or a single mode, fiber practical. Additionally, since, in preferred embodiments the excitation potential is time-varying, synchronous detection of weak fluorescent signals is possible. The electrical, spatial, and material characteristics of this air discharge scheme suggest its applicability to the rapid analysis of air samples by atomic and molecular emission spectroscopy or laser-induced fluorescence in the discharge channel. In particular, this device is well-suited for the detection of small concentrations of hazardous or toxic gases or vapors in atmospheric air.

Figure 2:
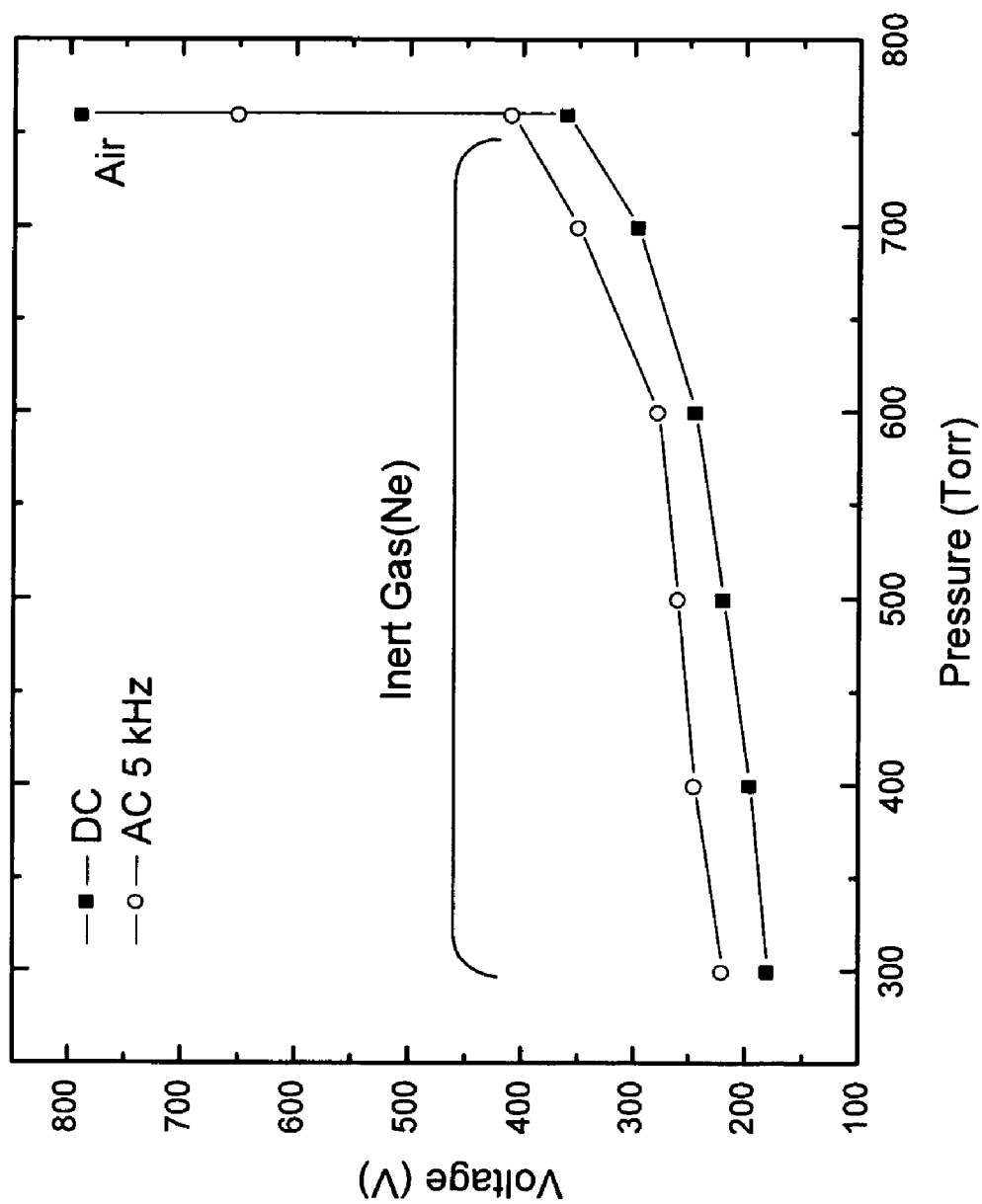
FIGS. 2 and 3 show voltage vs. current measurements for a prototype device consistent with FIG. 1 in various pressures of a noble gas and in air.
Figure 3:
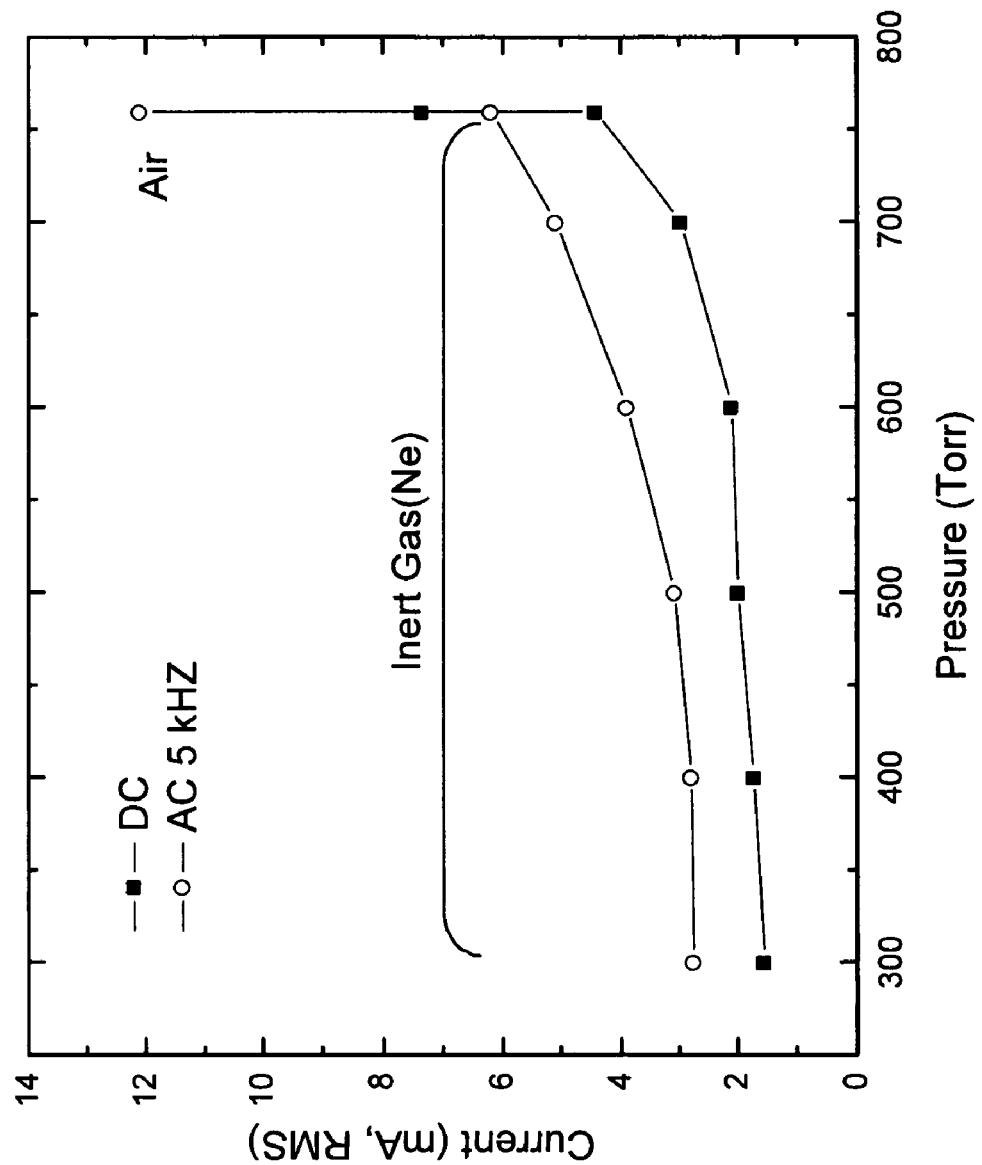

FIGS. 2 and 3 show voltage vs. current measurements for a prototype device consistent with FIG. 1 in various pressures of a noble gas and in air. While the voltages required for the plasma and the resulting current in a noble gas (Ne) are much lower than in air, the transverse dimensions of the plasma are large (thus resembling a plume) and diffusive. In atmospheric pressure air, the discharge is directional and confined—the discharge's cross-sectional dimensions are similar to the dimensions of the microcavity. The data of FIGS. 2 and 3 were acquired with a discharge device having a 50 μm×50 μm Si inverted pyramidal cavity and a probe electrode with a ~30 μm diameter tip. The distance between the cavity and the probe electrode was ~1 mm. A DC voltage between the excitation electrodes of the microdischarge device is also effective in producing a confined plasma within the microcavity and between the microcavity and the probe electrode (in this case, the probe electrode and device anode are at the same potential). However, preferred embodiments of the invention utilize an AC voltage because of its beneficial effect on device lifetime.

Figure 4:
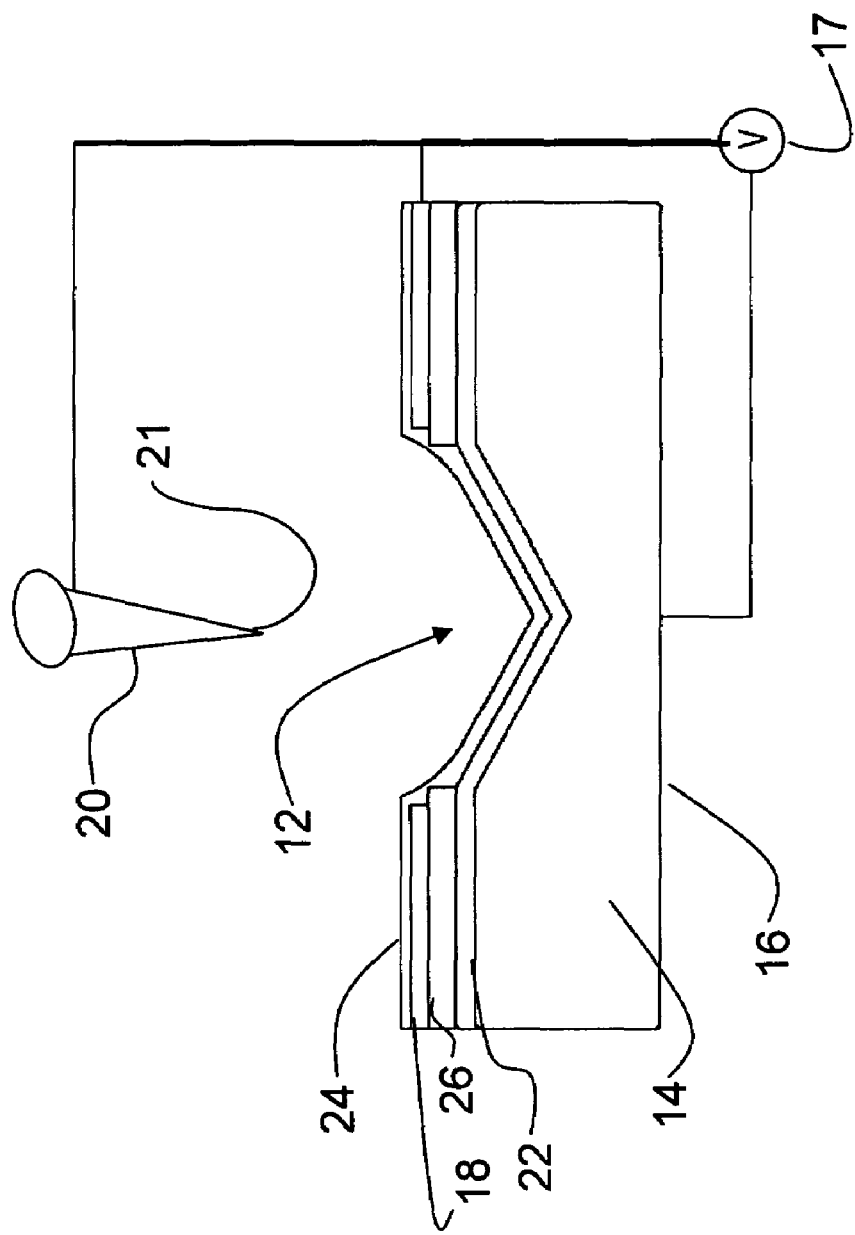
FIG. 4 is a perspective schematic view of another embodiment plasma extraction microcavity plasma device.

FIG. 4 shows an additional embodiment plasma extraction microcavity plasma device. In FIG. 4, reference numbers from FIG. 1 are used to identify comparable parts of the FIG. 4 device. A conducting (or semiconducting) substrate 14 is provided that includes a microcavity 12. The microcavity can extend to different depths, or even completely through the device. The substrate may be a semiconductor, such as a p-type wafer of Si ($\rho\sim$6-8 $\Omega$-cm), (where "$\rho$" is resistivity), a metal or a metal/polymer structure.

The microcavity 12 can be, for example, an inverted pyramidal microcavity that is etched in the substrate by wet processing. In other embodiments of the invention, a wide variety of microcavities having different cross-sectional geometries can be fabricated. A first dielectric layer 22 (typically 1 μm or more in thickness), which may be $Si_3N_4$ or $SiO_2$, is upon the substrate 14, preferably including the interior surface of the microcavity 12. A backside of the substrate forms an excitation electrode 16, which can be a direct contact to the substrate 14, or in other embodiments, can be another conductive or semiconductive layer.

Another excitation electrode 18 is disposed adjacent to the microcavity 12. In a specific embodiment of the invention, the excitation electrode 18 can be a conductor, such as Ni, deposited directly on the dielectric layer 22, adjacent to the microcavity 12 and a second dielectric layer 24, such as silicon nitride, can be formed on the second electrode 18, encapsulating the electrode and thereby prolonging the life of the device.

In additional embodiments of the invention, the second electrode can take on a variety of forms (screen, conducting polymer or semiconductor film, etc.). Electrodes in these forms can also be covered by one or more dielectric layers to further prolong the life of the device. Irrespective of the microcavity geometry chosen, minimizing the surface roughness of the cavity walls and the final dielectric surface within the microcavity is an important consideration.

In the embodiment of FIG. 4, an additional dielectric layer 26, such as polyimide, separates the dielectric layer 22 from the electrode 18. Moreover, an additional dielectric layer, such as silicon nitride, can be deposited onto any of the above described structures of the device, if desired. The device of FIG. 4 generates a plasma, which is extracted by the probe electrode 20 that is held to the potential of one of the electrodes 16, 18.

Additional embodiments use alternate microcavity plasma devices and arrays with the probe electrode 20 of FIGS. 1 and 4 disposed proximately the microcavity. Some preferred additional microcavity plasma devices that can be used with probe electrode to form a plasma extraction plasma device will be discussed and illustrated. Preferred embodiment microcavity plasma devices that can be used with a probe electrode to produce and extract a plasma are formed in a ceramic substrate that provides structure for an array of microcavities defined in the ceramic substrate. The ceramic substrate also electrically isolates the microcavities from electrodes buried within the ceramic substrate and physically isolates the microcavities from each other. The electrodes are buried within the ceramic substrate and disposed to ignite a discharge in microcavities in the array of microcavities upon application of a time-varying potential between the electrodes. Embodiments of the invention include electrode microcavity arrangements that permit addressing of individual microcavities or groups of microcavities. In preferred embodiments, address electrodes straddle or surround the microcavities. In other preferred embodiments, columns of microcavities are formed between pairs of substantially coplanar, parallel electrodes that are buried in the ceramic.

Figure 5:
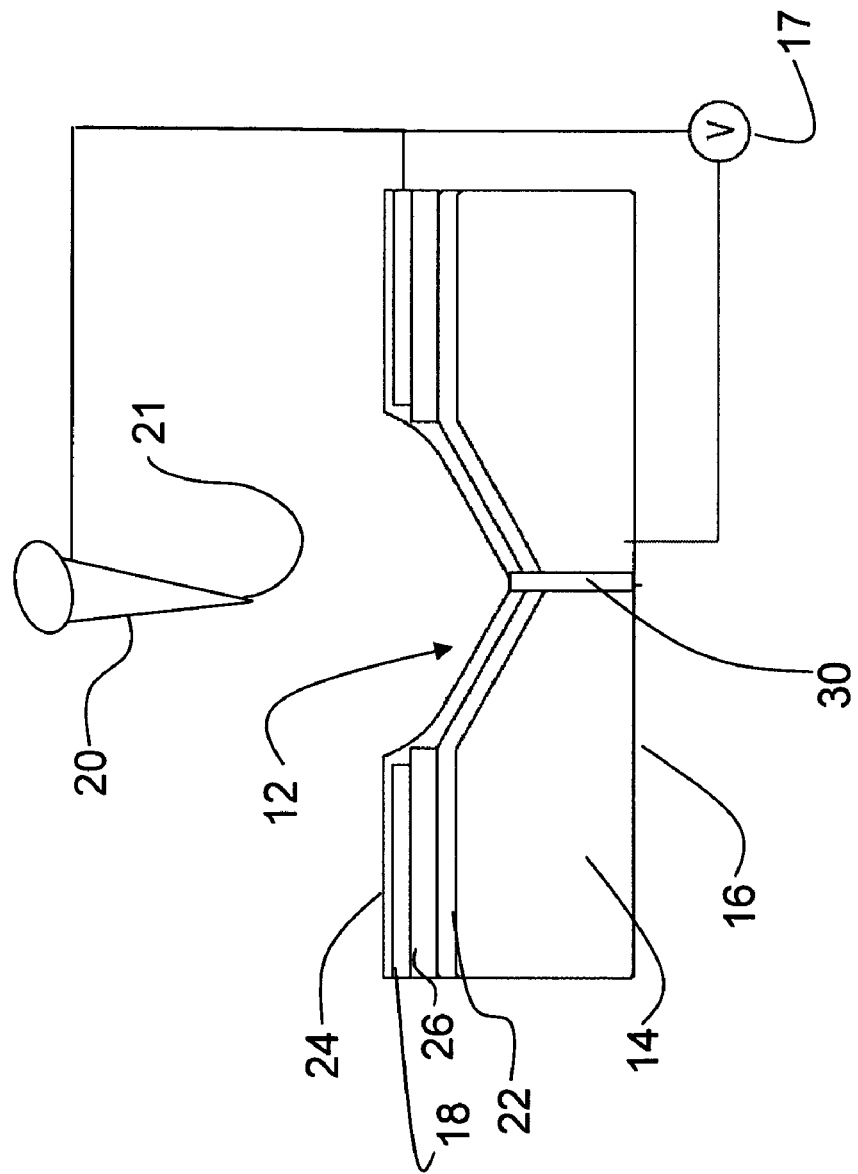
FIG. 5 shows an additional embodiment plasma discharge extraction microcavity plasma device.

FIG. 5 shows an additional embodiment that is similar to the embodiment of FIG. 4. Reference numbers from FIGS. 1 and 4 are used to identify comparable parts of the FIG. 4 device. The FIG. 5 device includes a gas feeding channel 30 that can feed discharge gas or vapor into the microcavity 12.

Figure 6:
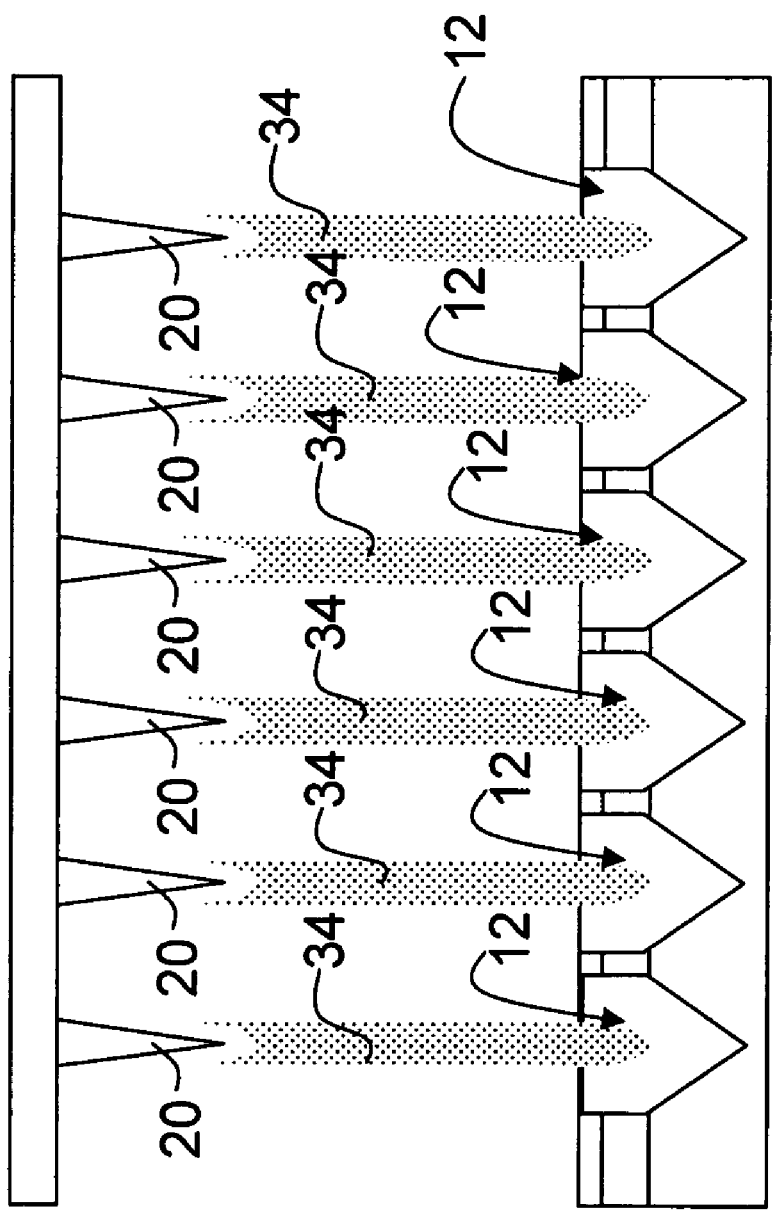
FIG. 6 shows an additional embodiment plasma discharge extraction microcavity plasma device.

FIG. 6 shows and additional embodiment device including an array of microcavities 12 and an array of probe electrodes 20. While illustrated schematically, each of the microcavities 12 and excitation electrodes associated therewith are preferably structured as in FIGS. 1, 4, or 5. Reference numbers from FIGS. 1, 4 and 5 are used to identify comparable parts of the FIG. 4 device. As shown in FIG. 6, an array of microcavities 12 and associated probe electrodes 20 can generate individual extraction columns 34 of plasma. Such an array has many applications. For example, the array of FIG. 6, can make an air plasma shower or a spatial diagnosis of element in large area by spectroscopic methods. Alignment is very accurate by semiconductor fabrication techniques, and optical properties from 2-D photonic crystal made by plasma can be demonstrated. In a preferred application, the discharge gas or vapor is noble or molecular gases having a specific emission in the range of UV~NIR.

Figure 7:
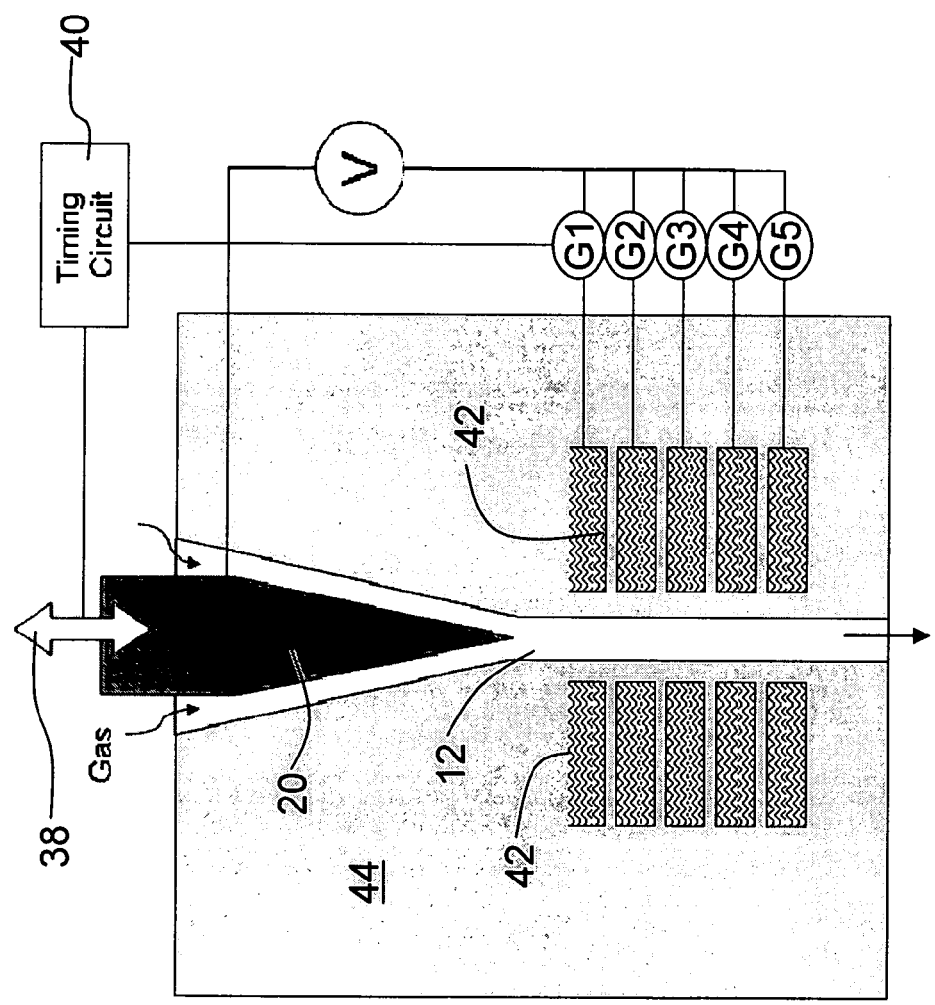
FIG. 7 shows an additional embodiment plasma discharge extraction microcavity plasma device.

FIG. 7 shows another preferred embodiment device. A probe electrode 20 is connected to a mover 38 controlled by a timing circuit 40. The movements of the electrode 20 can control gas flow in a microcavity 12 formed as an extended cavity with a plurality of excitation electrodes 42. The electrode 20 acts as a needle valve. A substrate 44 can be transparent. The electrodes 42 can be controlled by pulsed gate circuit that also has connected to the mover 38 of the probe electrode 20 through the timing circuit 40. With a movement of the needle (up and down- that is open and close of gas feeding channel), the pulsed potential is applied to the electrodes 20 sequentially. When one set of electrodes make a discharge with probe electrodes, others can make a discharge cascade at low voltage along the movement of desired discharge gases until they are expelled. During the specific discharge between one set of electrodes and the probe electrode, others electrodes remain in same potential with the probe or may float. This can be used, for example, for a micro-thruster or micro reactor having high efficiency. It can also be used for spectroscopy, for example. FIG. 8 shows an exemplary timing diagram, where P is the probe voltage and adjacent sets of electrodes 42 are labeled as cathode and anode.

While example microcavity plasma devices that can be used with a probe electrode as in FIGS. 1 and 4 have been described, artisans will recognize that other microcavity plasma devices, such as those known in the art and those that may be developed in the future can be used for plasma extraction in accordance with the invention.

In addition to known device, additional embodiment microcavity plasma devices are polymer microcavity devices that can be transparent, and can be rigid or flexible. Microcavity plasma device arrays of additional embodiments of the invention provide polymer microcavities that are readily mass fabricated, can be transparent, and can be rigid or flexible. Such devices and device arrays can also be used to generate a plasma and, with a probe electrode, extract a plasma.

A preferred embodiment of the invention is a microcavity plasma array formed in or on a transparent substrate and arranged proximately to a probe electrode 20. In preferred embodiments, microcavities are formed in a transparent material. Arrays of the invention can be very large format, as arrays of the invention can be produced by a highly accurate manufacturing processes that permits precision replication of microcavities.

Additionally, arrays of the invention can have high aspect ratio microcavities and channels. Microchannels in embodiments of the invention can connect microcavities, and have a wide variety of shapes, e.g., straight, zig-zig and other shapes.

Very long, high aspect ratio channels can be formed, e.g., a one meter channel that is 20 μm wide.

Another embodiment of the invention is a microchannel plasma device, with long, high aspect ratio optical channels arranged proximate a probe electrode. In a preferred embodiment, an optical microchannel plasma device has thin polymer walls separating microchannels. In a preferred embodiment, the polymer walls are transparent.

A fabrication method of the invention molds microcavities into a polymer material. Preferably, the polymer material is transparent. The mold is a negative volume profile of the microcavity shape, which can be, for example, cylindrical, pyramidal, truncated conical, or any other shape that can have its negative volume profile set in the mold. A flexible mold is preferably used to fabricate transparent polymer microcavities onto rigid substrates. A rigid mold is preferably used to fabricate transparent polymer microcativites onto flexible substrates. Having one of the mold and the substrate flexible and the other rigid aids separate of the mold from the cured polymer.

In an example embodiment, a mold is used to replicate microcavities into a liquid polymer material that can be cured into a solid state by exposure to UV light. The microcavity formation process is simple, rapid, and highly accurate. Further, the UV-curable polymer replication procedure is capable of producing deep cavities without the use of large forces or high temperatures, such as those required with stamping approaches. Producing microcavities of small transverse dimensions but large aspect ratio is also straightforward and inexpensive.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

The invention claimed is:

1. A plasma extraction microcavity plasma device, the device comprising:
    a substrate;
    a microcavity;
    excitation electrodes arranged by said substrate relative to said microcavity to excite a plasma in said microcavity when an appropriate voltage is applied across said excitation electrodes; and
    a probe electrode disposed proximate said microcavity and held to a substantially common voltage with respect to one of said excitation electrodes to extract plasma from said microcavity.

2. The device of claim 1, further comprising voltage source applied across said excitation electrodes.

3. The device of claim 1, wherein said excitation electrodes are isolated from said microcavity by dielectric.

4. The device of claim 1, wherein said microcavity comprises an array of microcavities.

5. The device of claim 1, wherein said substrate comprises a ceramic substrate.

6. The device of claim 1, wherein said microcavity is formed in polymer.

7. The device of claim 1, wherein said microcavity comprises a microchannel.

8. The device of claim 1, wherein the probe electrode has a dielectric tip.

9. The device of claim 1, wherein the probe electrode comprises a semiconductor.

10. The device of claim 1, wherein a gap from a tip of the probe electrode to the microcavity is in the range of approximately 100 μm to 1.0 mm.

11. The device of claim 1, wherein the microcavity has one of a trapezoidal, rectangular, and cylindrical cross-section.

12. The device of claim 1, wherein said probe electrode comprises an array of probe electrodes.

13. The device of claim 1, further comprising a mover for moving said probe electrode relative to said microcavity.

14. A method for producing and extracting a plasma, the method comprising steps of:
    in the presence of one of a gas, vapor, and gas and vapor, disposing a microcavity plasma discharge device;
    applying an appropriate voltage across excitation electrodes of the microcavity plasma discharge device to produce a plasma within a microcavity of the microcavity plasma discharge device;
    holding the tip of a probe electrode disposed proximate to the microcavity to the substantially the same voltage as one of the excitation electrodes to extract the plasma from the microcavity.

15. The method of claim 14, wherein the microcavity plasma device is disposed in atmospheric pressure air and the plasma is produced and extracted in the atmospheric pressure air.

16. The method of claim 14, wherein a gap from a tip of the probe electrode to the microcavity is in the range of approximately 100 μm to 1.0 mm.

* * * * *

UNITED STATES PATENT AND TRADEMARK OFFICE
CERTIFICATE OF CORRECTION

PATENT NO. : 7,482,750 B2
APPLICATION NO. : 11/344514
DATED : January 27, 2009
INVENTOR(S) : Eden et al.

It is certified that error appears in the above-identified patent and that said Letters Patent is hereby corrected as shown below:

Col. 5, Line 47   Please delete "microplasmascan" and insert --microplasmas can-- in its place.

Col. 8, Line 1    Please delete "and" and insert --an-- in its place.

Signed and Sealed this

Ninth Day of June, 2009

JOHN DOLL
*Acting Director of the United States Patent and Trademark Office*